US00PP11210P

United States Patent [19]

VandenBerg

[11] Patent Number: Plant 11,210

[45] Date of Patent: Feb. 8, 2000

[54] CHRYSANTHEMUM PLANT NAMED 'YOTOPEKA'

[75] Inventor: Cornelis P. VandenBerg, Salinas, Calif.

[73] Assignee: Yoder Brothers, Inc., Barberton, Ohio

[21] Appl. No.: 09/112,334

[22] Filed: Jul. 9, 1998

[51] Int. Cl.[7] ..... A01H 5/00

[52] U.S. Cl. ..... Plt./289

[58] Field of Search ..... Plt./289

*Primary Examiner*—Howard J. Locker

*Attorney, Agent, or Firm*—C. A. Whealy

[57] ABSTRACT

A distinct cultivar of Chrysanthemum plant named 'Yotopeka', characterized by its upright and uniformly mounded plant habit; freely branching habit; uniform and early flowering; large decorative disbud-type inflorescences that are about 9 cm in diameter; attractive yellow-colored ray florets; and good postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yotopeka. The plant is being marketed under the name Topeka.

The new Chrysanthemum is a product of a planned breeding program conducted by the inventor in Salinas, Calif. The objective of the breeding program is to create new pot-type Chrysanthemum cultivars having desirable inflorescence forms and floret colors and excellent post-production longevity.

The new Chrysanthemum originated from a cross made by the breeder in September, 1993, in Salinas, Calif., of the commercial Chrysanthemum cultivar Delano (disclosed in U.S. Plant Pat. No. 6,950) as the male, or pollen, parent with the commercial Chrysanthemum cultivar Pomona (disclosed in U.S. Plant Pat. No. 6,802) as the female, or seed, parent.

The new Chrysanthemum was discovered and selected by the inventor as a flowering plant within the progeny of the stated cross in a controlled environment in Salinas, Calif., in December, 1994. The selection of this plant was based on its desirable inflorescence form and floret colors and good post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Yotopeka has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yotopeka'. These characteristics in combination distinguish 'Yotopeka' as a new and distinct Chrysanthemum:

1. Uniformly mounded plant habit.
2. Freely branching habit, dense plants.
3. Very dark green foliage.
4. Uniform and early flowering.

5. Relatively large decorative disbud-type inflorescences that are about 9 cm in diameter.
6. Attractive bright yellow-colored ray florets.
7. Good postproduction longevity with inflorescences and leaves maintaining good substance and color for about three or four weeks in an interior environment.

The new Chrysanthemum can be compared to the Chrysanthemum cultivar Sunray, not patented. However in side-by-side comparisons in Salinas, Calif., and Leamington, Ontario, Canada, under commercial practice, plants of the new Chrysanthemum differed from plants of the cultivar Sunray in the following characteristics:

1. Plants of the new Chrysanthemum are taller and larger than plants of the cultivar Sunray.
2. Plants of the new Chrysanthemum are more freely branching and therefore more floriferous than plants of the cultivar Sunray.
3. Plants of the new Chrysanthemum have larger leaves than plants of the cultivar Sunray.
4. Plants of the new Chrysanthemum flower more uniformly than plants of the cultivar Sunray.
5. Plants of the new Chrysanthemum flower one or two days earlier than plants of the cultivar Sunray.
6. Plants of the new Chrysanthemum have larger and taller inflorescences than plants of the cultivar Sunray.
7. Plants of the new Chrysanthemum have more numerous ray florets than plants of the cultivar Sunray.

A detailed comparison of plants of the new Chrysanthemum and the cultivar Sunray appears in Chart A at the end of the specification.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yotopeka'.

The photograph at the bottom of the first sheet is a close-up view of a typical inflorescence of a plant of 'Yotopeka'.

The photograph at the top of the second sheet is a close-up view of upper and lower surfaces of typical inflorescences (top) and leaves (bottom) of plants of 'Yotopeka'.

The photograph at the bottom of the second sheet comprises a side perspective view of typical plants of 'Yotopeka' (left) and 'Sunray' (right) showing the differences in plant size and floriferousness. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Yotopeka.

Commercial classification: Decorative disbud-type pot chrysanthemum.

Parentage:

*Male or pollen parent.*—*Dendranthema grandiflora* cultiar Delano, disclosed in U.S. Plant Pat. No. 6,950.

*Female or seed parent.*—*Dendranthema grandiflora* cultivar Pomona, disclosed in U.S. Plant Pat. No. 6,802.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative disbud-type pot Chrysanthemum. Upright, inverted triangle. Stems initially upright, then somewhat spreading giving a uniformly mounded appearance to the plant. Freely branching; about four lateral branches develop after removal of terminal apex (pinching), dense and full plants.

*Plant height.*—Tall, about 29 cm.

*Plant width.*—About 40 cm.

*Stem color.*—143A.

*Foliage description.*—Arrangement: Alternate. Length: About 7.8 cm. Width: About 4.8 cm. Apex: Mucronate. Base: Attenuate to truncate. Margin: Palmately lobed, sinuses between lateral lobes parallel to converging. Texture: Upper and lower surfaces slightly pubescent, very fine white hairs. Veins prominent on lower surface. Petiole length: About 1.7 cm. Color: Young foliage upper surface: Darker than 147A. Young foliage lower surface: Darker than 147B. Mature foliage upper surface: 147A. Mature foliage lower surface: Slightly darker than 147B. Venation upper surface: 147A to 147B. Venation lower surface: 147B.

Inflorescence description:

*Appearance.*—Decorative disbud-type inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescences and leaves will maintain good color and substance for about three or four weeks in an interior environment.

*Quantity of Inflorescences.*—As a disbud-type, all flowering stems are removed but one to maximize inflorescence size. About four inflorescences per plant.

*Inflorescence bud.*—Height: About 7 mm. Diameter: About 9 mm. Color: Greener than 137A.

*Inflorescence size.*—Diameter: About 9 cm. Depth (height): About 3.4 cm. Diameter of disc: About 4.5 mm, inconspicuous.

*Ray florets.*—Shape: Oblong with very short corolla tube. Aspect: Straight, flat. Length: About 4.5 cm. Width: About 1.3 cm. Apex: Rounded to emarginate. Margin: Entire. Texture: Smooth, glabrous. Number of ray florets per inflorescence: Numerous, about 185. Color: When opening, upper surface: 5A. When opening, lower surface: 5A. Fully opened, upper surface: 5A to 3A to 3B. Fully opened, lower surface: 3B to 3C to 3D.

*Disc florets.*—Shape: Tubular. Apex: Dentate. Length: About 7.5 mm. Width: Apex: About 2.5 mm. Base: About 1 mm. Number of disc florets per inflorescence: Few, about 16. Color: Immature: Yellowish green. Mature: Apex: 7A. Mid-section and base: White.

*Reproductive organs.*—Androecium: Present on disc florets only. Anther color: 9A. Pollen: Amount: Moderate to low. Color: 9A. Gynoecium: Present on both ray and disc florets.

Disease resistance: No known Chrysanthemum diseases observed to date on plants grown under commercial greenhouse conditions.

Seed production: Seed production has not been observed.

CHART A

| CHARACTERISTIC | 'YOTOPEKA' | 'SUNRAY' |
|---|---|---|
| PLANT HEIGHT | About 29 cm | About 25 cm |
| PLANT WIDTH | About 40 cm | About 36 cm |
| LEAF LENGTH | About 7.8 cm | About 6.9 cm |
| LEAF WIDTH | About 4.8 cm | About 4.5 cm |
| INFLORESCENCE DIAMETER | About 9 cm | About 8 cm |
| INFLORESCENCE HEIGHT | About 3.4 cm | About 3 cm |
| RAY FLORET LENGTH | About 4.5 cm | About 4.2 cm |
| RAY FLORET WIDTH | About 1.3 cm | About 1.2 cm |

It is claimed:

1. A new and distinct cultivar of Chrysanthemum plant named 'Yotopeka', as illustrated and described.

* * * * *

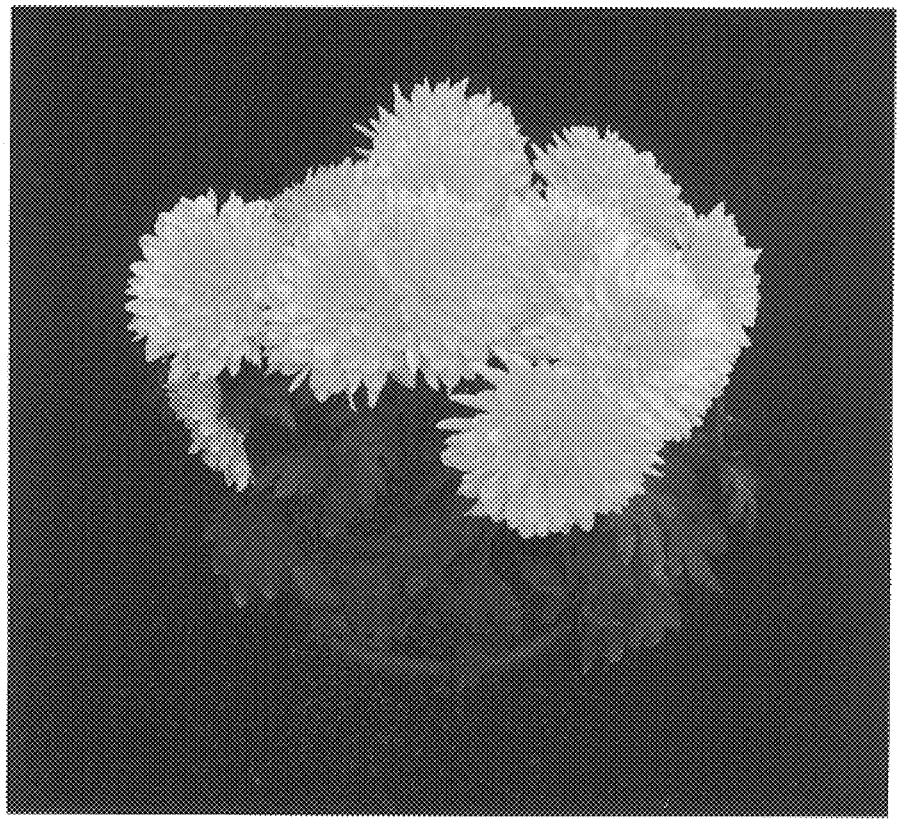
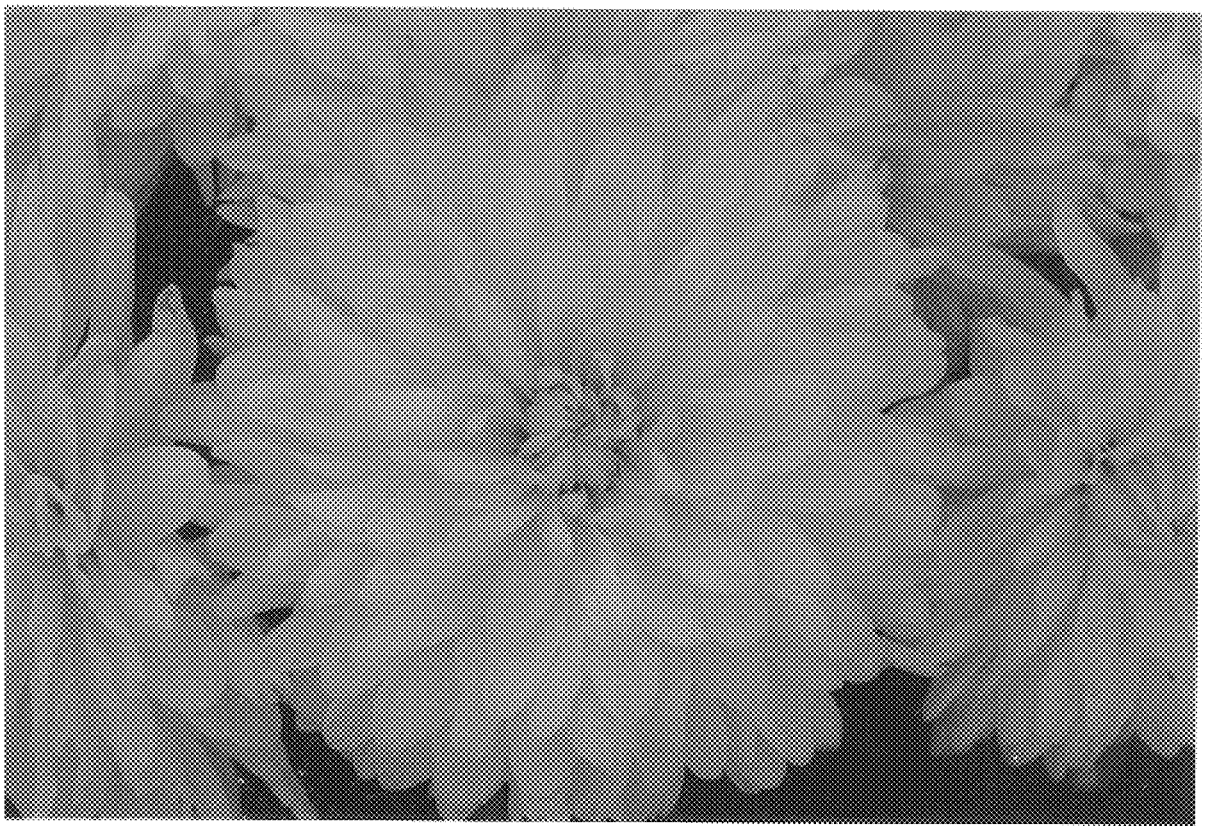

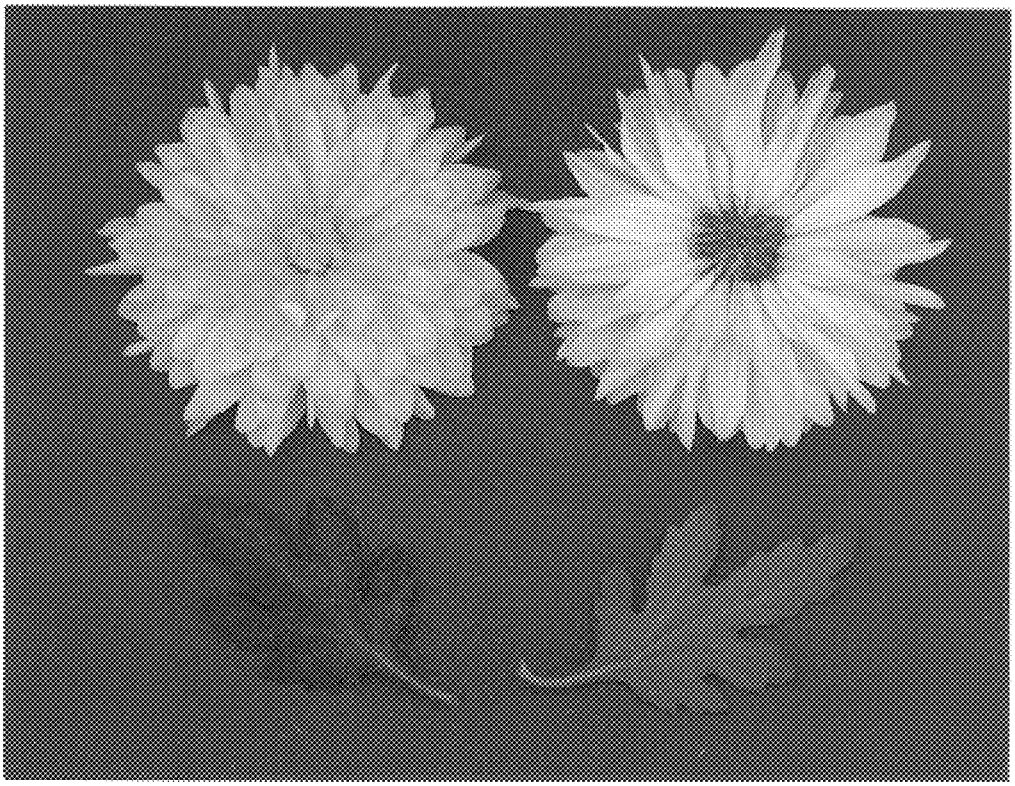
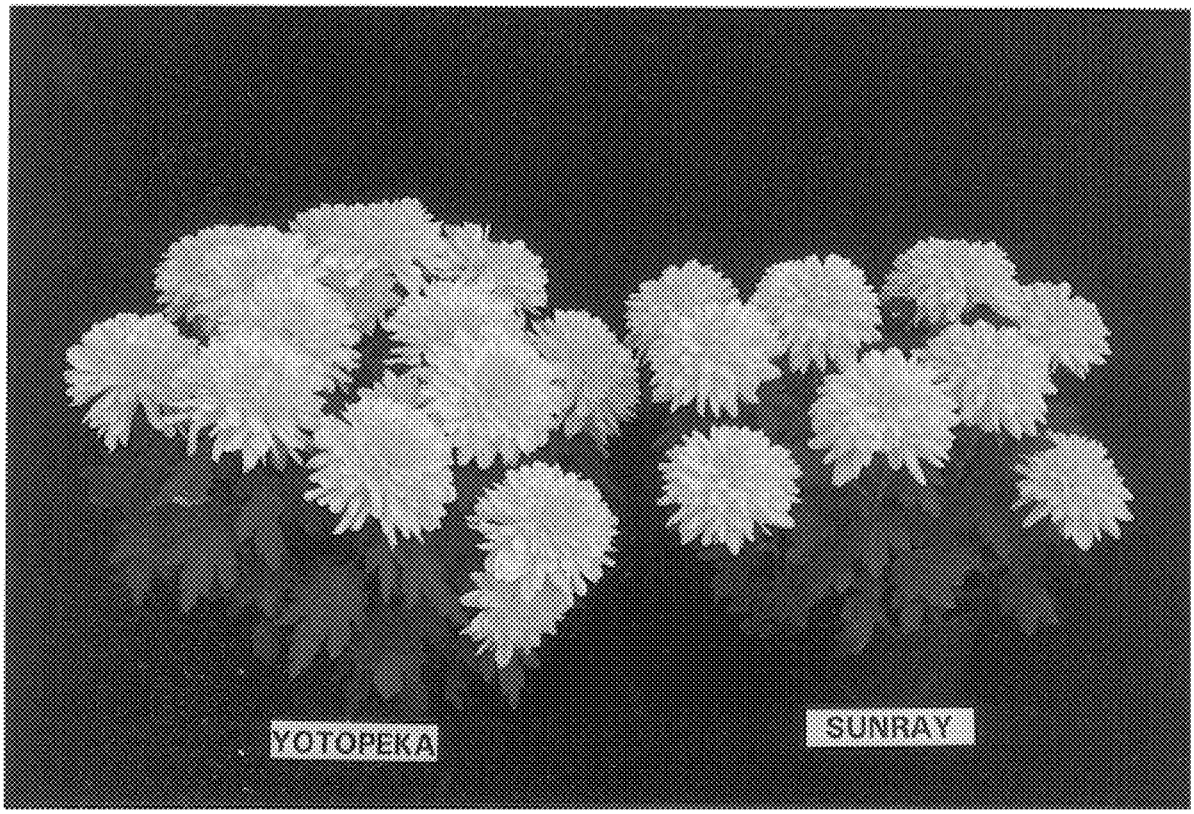
YOTOPEKA
SUNRAY